April 17, 1934. M. GERBER Plant Pat. 94
CHERRY
Filed June 29, 1932
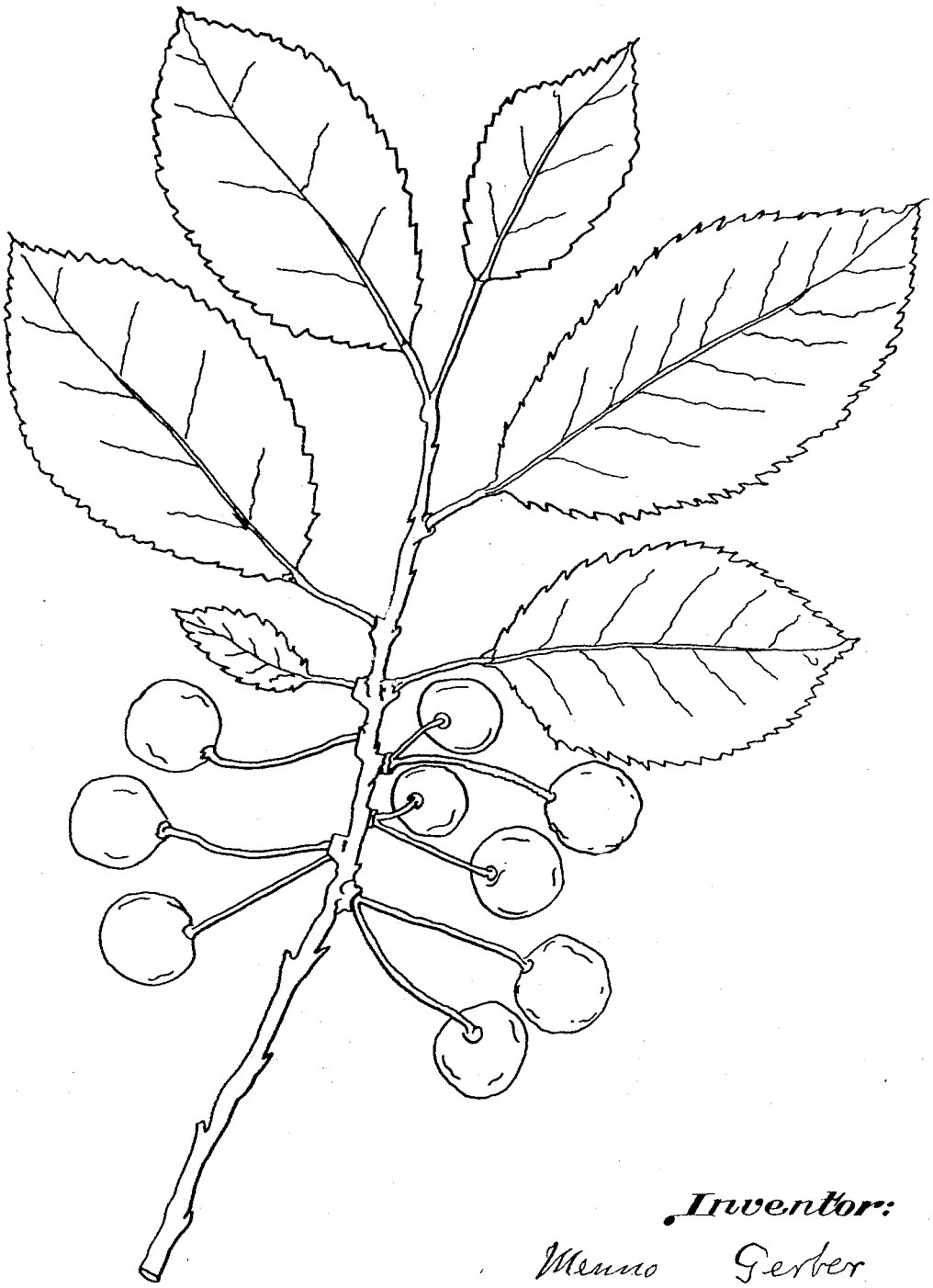
Inventor:
Menno Gerber
By Hiram B. Swartz Atty.

Patented Apr. 17, 1934

Plant Pat. 94

UNITED STATES PATENT OFFICE

94

CHERRY

Menno Gerber, Orville, Ohio

Application June 29, 1932, Serial No. 620,053

1 Claim. (Cl. 47—62)

My invention relates to cherry tree and fruit of late ripening variety, discovered and asexually reproduced by me, the fruit thereof ripening when the usual varieties have finished bearing.

The original tree is located on a farm in Holmes County, Ohio. All other cherry trees in the same locality of about the same age are of the earlier ripening variety. None of them equals this tree in size or denseness of foliage and length of leaves or lateness of ripening of its fruit, which occurs about two months after all other varieties have ripened and disappeared.

I first discovered this tree about four years ago, and have since propagated about a dozen young trees by the usual means of grafting or budding. These young trees appear to be more thrifty in growth and fruitage than same age trees of the ordinary varieties. The distinctive features of the original tree remain the same on said young trees. The original tree is still bearing fruit.

The drawing illustrates a branch and fruit in black and white because color is not necessary, as the main distinction relates to the ripening of its fruit after all other varieties have left the market.

The following is a technical description of the original tree and its fruit—

The tree is about forty five years old, and is unusually large, having two trunks, each spreading to about 15 feet in diameter, upright, thrifty and highly productive. Branches smooth, dull reddish brown, with numerous lenticels; branchlets thick, long, dark reddish brown, mostly covered with ash gray, smooth, glabrous, with few lenticels.

*Leaves.*—Resinous at opening; when mature, about 4½ inches long, 2⅓ inches wide, folded upward, oval to obovate, medium thin; upper surface medium green, smooth, lower surface light green, lightly pubescent; apex acute, base abrupt, sometimes heart shaped; margin doubly serrate, glandular; petiole 1¼ to 1½ inches long, dull red, pubescent, usually two—more or less kidney shaped, reddish colored glands on the stalk.

*Flower.*—Season of bloom normal mid-season—full bloom May 2nd, 1933; flowers white, about 1¼ inches across, borne usually in twos or threes, sometimes singly; pedicels about 2 inches long, slender, glabrous, green; calyx tube green faintly tinged with red, long, medium broad, reflexed; petals oval to roundish, entire, crenate; filaments of different lengths, the longest about ½ inch; pistil glabrous, shorter than a few, equal with some, and longer than many of the stamens.

*Fruit.*—Cherry from ⅝ to 6/8 inches wide, ⅝ to 6/8 inches long; roundish, cordate; cavity medium deep, slightly flaring; suture shallow, often a mere line; apex roundish, depressed at center; color light to medium red; dots obscure; stem tinged with red, 1¾ to 2 inches long, adherent to fruit; skin thin, adherent to pulp; flesh yellowish to light red, with light juice, firm pleasant flavored, sweet.

*Stone.*—Clinging, small—somewhat flattened, blunt, oblique, with smooth surface, somewhat ridged along the ventral suture, tinged with pink. The fruit is very firm and robust, and excellent for canning—sweet and very palatable when fully ripe. The length of the fruit stem is longer than that of standard varieties, and the time from bloom to ripe fruit is longer than any other variety of cherries known.

I claim:

The cherry tree and fruit as described, said tree bearing its fruit when and after all other varieties have finished bearing.

MENNO GERBER.